US009221752B2

(12) United States Patent
Kim et al.

(10) Patent No.: US 9,221,752 B2
(45) Date of Patent: Dec. 29, 2015

(54) SYNTHESIS OF MOLECULAR SIEVES FOR MODIFYING THE SURFACES OF NANOPARTICLES HAVING AMPHOTERIC IONS, AND APPLICATION THEREOF

(75) Inventors: Sungjee Kim, Gyungbuk (KR); Joonhyuck Park, Gyungbuk (KR); Jutaek Nam, Gyungbuk (KR); Ho Jin, Chungnam (KR)

(73) Assignee: Postech Academy-Industry Foundation, Gyungbuk (KR)

( * ) Notice: Subject to any disclaimer, the term of this patent is extended or adjusted under 35 U.S.C. 154(b) by 55 days.

(21) Appl. No.: 13/881,844

(22) PCT Filed: Oct. 28, 2011

(86) PCT No.: PCT/KR2011/008116
§ 371 (c)(1),
(2), (4) Date: Jun. 25, 2013

(87) PCT Pub. No.: WO2012/057556
PCT Pub. Date: May 3, 2012

(65) Prior Publication Data
US 2014/0051883 A1    Feb. 20, 2014

(30) Foreign Application Priority Data

Oct. 29, 2010    (KR) ........................ 10-2010-0106731

(51) Int. Cl.
*C07C 323/41*    (2006.01)
*B82B 1/00*    (2006.01)
*C07C 319/06*    (2006.01)

(52) U.S. Cl.
CPC ............... *C07C 323/41* (2013.01); *B82B 1/005* (2013.01); *C07C 319/06* (2013.01)

(58) Field of Classification Search
None
See application file for complete search history.

(56) References Cited

U.S. PATENT DOCUMENTS

| 7,785,392 | B2 | 8/2010 | Shim et al. |
| 2007/0275259 | A1 | 11/2007 | Lee et al. |
| 2009/0202816 | A1 | 8/2009 | Schlenoff |

FOREIGN PATENT DOCUMENTS

| KR | 10-2006-0021535 | 3/2006 |
| KR | 100555594 B1 | 3/2006 |

(Continued)

OTHER PUBLICATIONS

Park et al., Advanced Functional Materials (2011), 21(9), 1558-1566, first published online: Feb. 11, 2011, DOI: 10.1002/adfm. 201001924.*

(Continued)

*Primary Examiner* — Karl J Puttlitz
(74) *Attorney, Agent, or Firm* — Thompson Hine LLP

(57) ABSTRACT

The present invention relates to a surface modification method for improving the dispersion of nanoparticles, and to nanoparticles having improved dispersion properties prepared by the method. More particularly, the present invention relates to a method in which amphoteric compounds are bonded to the surfaces of nanoparticles to improve dispersion at the surfaces of nanoparticles. The present invention also relates to nanoparticles using the method. Both anions and cations are formed on the surfaces of the nanoparticles according to the present invention, and therefore the nanoparticles are electrically stable so as to achieve stability in a wide pH range, are stably dispersed in the event of a high concentration of salts, and the non-specific adsorption thereof is reduced. Novel specific substances or sensors having minimized non-specific adsorption may be produced using the nanoparticles of the present invention.

13 Claims, 8 Drawing Sheets

(56) References Cited

FOREIGN PATENT DOCUMENTS

| KR | 100724807 B1 | 5/2007 |
| KR | 100820231 B1 | 4/2008 |
| KR | 20080081630 A | 9/2008 |
| KR | 100861355 B1 | 10/2008 |
| WO | 2010/076237 A2 | 7/2010 |

OTHER PUBLICATIONS

PCT International Search Report, PCT/KR2011/008116 (mailed Feb. 2, 2012), 3 pages.
Winzell. Surface Modification of CdSe(ZnS) quantum dots for biomedical applications. Master's Thesis, Department of Physics, Chemistry, and Biology, Linköping University Institute of Technology, Feb. 15, 2010 (69 pages).
Yang et al. Functionalizable and ultra stable nanoparticles coated with zwitterionic poly(carboxybetaine) in undiluted blood serum. Biomaterials, vol. 30 (2009), pp. 5617-5621.
Supplementary European Search Report EP 11 83 6648, Oct. 15, 2014, 2 pages.
D1 CN Winzell. Surface Modification of CdSe(ZnS) quantum dots for biomedical applications. Masters Thesis, University of Washington Feb. 15, 2010 (18 pages).
D1 ESR Pons et al. Hydrodynamic sizes of functional hydrophilic QDs. Colloidal Quantum Dots for Biomedical Applications, Eds. Marek Osinski et al., Proc. of SPIE vol. 6096, 60961 H, (2006) (10 pages).
Park et al. Compact and Stable Quantum Dots with Positive, Negative, or Zwitterionic Surface: Specific Cell Interactions and Non-Specific Adsorptions by the Surface Charges. Adv. Funct. Mater. (2011), 21, 1558-1566.

\* cited by examiner

QUANTUM DOT
SURFACE-SUBSTITUTED
AMPHOTERIC ION MOLECULE

QUANTUM DOT
SURFACE-SUBSTITUTED
CARBOXYLIC ACID MOLECULE

SYNTHESIS OF MOLECULAR SIEVES FOR MODIFYING THE SURFACES OF NANOPARTICLES HAVING AMPHOTERIC IONS, AND APPLICATION THEREOF

RELATED APPLICATIONS

This application is a National Phase of co-pending International Application No. PCT/KR2011/008116 filed Oct. 28, 2011 which claims priority to Korean Patent Application No. KR 10-2010-0106731 filed Oct. 29, 2010.

TECHNICAL FIELD

The present invention relates to a surface modification method for improving the dispersion of nanoparticles and to nanoparticles having improved dispersion properties prepared by the method. More particularly, the present invention relates to a method of improving the surface dispersion of nanoparticles by bonding amphoteric compounds to the surface of nanoparticles and to nanoparticles prepared using the method.

BACKGROUND ART

There have been proposed various methods for preparing nanoparticles. Among these methods, flame pyrolysis, spray pyrolysis, a sol-gel process, a solvothermal method and the like, as well as transitional physical pulverizing methods, have been used. In the process of forming nanoparticles, nanoparticles are formed and simultaneously agglomerated because the surface of a nanoparticle is unstable. Therefore, methods for overcoming the agglomeration of nanoparticles have been developed.

Korean Unexamined Patent Application Publication No. 2008-0004831 (applicant: Samsung Electro-Mechanics Co., Ltd.) discloses a method of preparing metal oxide nanoparticles stabilized by covering the surface of a copper precursor with capping molecules, and metal oxide nanoparticles prepared by this method. Korean Patent No. 820231 (patentee: Samsung Electro-Mechanics Co., Ltd.) discloses a method of preparing metal nanoparticles by spray-injecting a metal precursor solution. Korean Patent No. 790948 (patentee: Samsung Electro-Mechanics Co., Ltd.) discloses a method of preparing metal nanoparticles using a metal precursor solution and a dispersion stabilizer.

Korean Patent No. 790948 (patentee: Sungkyunkwan University Academy-industry Foundation) discloses a method of preparing nanoparticles using an electroless plating solution. Korean Unexamined Patent Application Publication No. 2008-81630 (applicant: Korean Institute of Industrial Technology (KITECH)) discloses a method of preparing nanoparticles by spraying an electroless plating solution on a substrate.

Korean Patent No. 555584 (inventor: Choi Yong-ho) discloses a method of preparing metal nanoparticles using electrolysis. Korean Patent No. 724807 (patentee: Korea University Academy-industry Foundation) discloses a method of preparing tin oxide nanoparticles using oleic acid and tin oxide nanoparticles prepared by this method.

Further, there have also been proposed methods of stabilizing nanoparticles by introducing a ligand such as amine or sodium ascorbate into the nanoparticles to fix the nanoparticles on active carbon, an inorganic oxide, a polymer, zeolite or the like. Korean Unexamined Patent Application Publication No. 10-2008-0021535 (applicant: Yonsei University) discloses a method of modifying the surface of nanoparticles using a multifunctional ligand and a method of preparing water-soluble nanoparticles.

Since nanoparticles stably dispersed in an aqueous solution receive a great deal of attention in the field of biological engineering and medical engineering, the demand thereof is very high internally and externally. Therefore, various technologies for stably dispersing nanoparticles in an aqueous solution have been continuously researched in various manners, and it has been continuously required to develop novel, uniform and stable nanoparticles, and preparation methods thereof.

DISCLOSURE

Technical Problem

An object of the present invention is to provide a novel nanoparticle which is stable in a wide pH range and in a wide salt concentration range.

Another object of the present invention is to provide a method of preparing a novel nanoparticle which is stable in a wide pH range and in a wide salt concentration range.

Still another object of the present invention is to provide a modification method of improving the stability of a nanoparticle.

Still another object of the present invention is to provide a new compound which can improve the stability of a nanoparticle.

Still another object of the present invention is to provide a novel quantum dot which has stability in a wide pH range and in a wide salt concentration range and to provide an application thereof.

Technical Solution

In order to accomplish the above objects, the nanoparticle according to the present invention may be an amphoteric nanoparticle including both an anion and a cation on the surface thereof.

Although not theoretically limited, the nanoparticle according to the present invention acts as a stable nanoparticle because amphoteric ion molecules are more slightly influenced by a charge shielding effect due to ions under the conditions of a wide pH range and a high salt concentration, compared to molecules having only a positive charge or a negative charge.

In the present invention, the nanoparticle refers to a nano-sized particle having a diameter of less than 1000 nm. In an embodiment of the present invention, according to the nanoparticle defined by the National Science Foundation, the nanoparticle has a diameter of 300 nm or less. In another embodiment of the present invention, according to the nanoparticle defined by the National Institute of Health, the nanoparticle has a diameter of 100 nm or less.

In the present invention, the nanoparticle may be made of a metal, a nonmetal, ceramic, plastic, a polymer, a biological material, a semiconductor, a quantum dot, a composite material, or the like. Further, the nanoparticle may be a fluorescent nanoparticle. The composite material may be a particle including a core made of a nonmetal material such as a ceramic or a polymer and coated with a metal.

In the present invention, the nanoparticle may be formed into one nanoparticle or one nanoparticle assembly due to agglomeration of several metal nanoparticles. The nanoparticle may be a high-density nanoparticle whose inside is filled, or a nanoparticle including a compartment or space therein. In an embodiment of the present invention, the nanoparticle may be a monolayered nanoparticle or a multilayered nanoparticle.

In the present invention, a neutral nanoparticle refers to a substantially neutral nanoparticle in which anions and cations are balanced with each other. Further, in the present invention, the neutral nanoparticle refers to a nanoparticle having a surface charge of −5 mV to +5 mV, which is measured by dynamic light-scattering photometry, and the absolute value of the surface charge does not exceed 10 mV.

In an aspect of the present invention, the nanoparticle is an amphoteric nanoparticle whose surface is bonded with amphoteric ion molecules or amphoteric ion compounds.

In the present invention, the amphoteric ion molecule or the amphoteric ion compound is a compound including one or more anions and one or more cations. Further, in the present invention, the amphoteric ion molecule or the amphoteric ion compound may be a monomer, an oligomer such as dimer, trimer or the like, or a polymer. Preferably, when the length of the amphoteric ion molecule is smaller than the outer diameter of the nanoparticle, the amphoteric ion molecule does not surround the nanoparticle, and thus the amphoteric ion molecules are bonded with the nanoparticle in a direction from the center of the nanoparticle toward the outside thereof, and, as a result, amphoteric ions are distributed on the outermost surface of the nanoparticle.

In the present invention, as shown in FIG. 1, the amphoteric ion compound may include a surface bonding region bonded with a nanoparticle, a connecting region, and a functional group region. Preferably, the amphoteric ion compound may be configured such that one end thereof is bonded with a nanoparticle and the other end thereof is provided with amphoteric ions.

In an embodiment of the present invention, the surface bonding region is strongly bonded with the surface of a nanoparticle, and can be used without limitation as long as it can be stably bonded with the nanoparticle. Examples of the surface bonding region may include, but are not limited to, a thiol group (—SH), dithiol groups (—$CS_2$, —$PS_2$, —CH(SH)($CH_2CH_2SH$)), amine groups (—$NH_2$, —NH), a phosphonate group (—$PO_3H$), a phosphide group (—P), a phosphine oxide group (—P=O), a carboxy group (—COOH), a hydroxy group (—OH), an imidazole group, a diol group, and the like.

In the present invention, the connecting region serves to effectively connect the surface bonding region with the functional group region. Examples of the connecting region may include, but are not limited to, an amide bond (—CONH—), a carbon bond (—$(CH_2)_n$—), polyethylene glycol (—$(CH_2CH_2O)_n$—), triazole, and the like. In an embodiment of the present invention, the connecting region may be formed by bonding two or more molecules, and preferably may be configured such that the surface of the nanoparticle is entirely coated with molecules in high density.

In the present invention, the functional group region has an ability to stably disperse nanoparticles in a solvent, and is chemically bonded with the connecting region. An amphoteric ion is used as the functional group region. Examples of the amphoteric ion may include, but are not limited to, a sulfobetaine group (—$N^+(CH_3)_2CH_2CH_2CH_2SO^{3-}$), a carbobetaine group (—$N^+(CH_3)_2CH_2CH_2CH_2COO^-$), a phosphorylcholine group (—$PO_4^-CH_2CH_2N^+$) and the like. The functional group region is revealed on the outermost surface of the nanoparticle surface-substituted with an amphotric ion molecule, and thus this nanoparticle may have characteristics of the amphoteric ion molecule itself.

In an embodiment of the present invention, cysteine is one of many monomers that are constituents of proteins, that is, one of many amino acids that are constituents of proteins, and has a thiol group (—SH) at one side thereof and a carboxylic acid group (—$COO^-$) and an amine group (—$NH_3^+$) at the other side thereof. The thiol group (—SH) of cysteine becomes a surface bonding region bonded with a nanoparticle, and the carboxylic acid group (—$COO^-$) and amine group (—$NH_3^{+/}$) of cysteine become a functional group region. Consequently, in the nanoparticle surface-treated with cysteine, cysteine serves as an amphoteric ion molecule at a pH of about 7, thus making a surface charge approximately neutral.

In an aspect of the present invention, there is provided a method of preparing an amphoteric ion nanoparticle by reacting a nanoparticle with amphoteric ion molecules.

In an embodiment of the present invention, the amphoteric ion nanoparticle may be prepared by a process including the steps of: introducing surface molecules (for example, ligands) that can be substituted with amphoteric ion molecules onto the surface of the nanoparticle; and substituting the surface molecules with amphoteric ion molecules.

In an aspect of the present invention, there is provided a method of controlling a nonspecific adsorption of a nanoparticle by forming amphoteric ion molecules on the surface of a nanoparticle.

Here, the term "nonspecific adsorption" refers to adsorption caused by ion bonding, intermolecular attraction or the like, and excludes specific bonding between a nanoparticle and an external material or between a material included in the nanoparticle and an external material.

Here, the term "control" means that the adsorptivity of a nanoparticle is reduced under a specific condition after amphoteric ion molecules are formed on the surface of the nanoparticle.

Although not theoretically limited, since the surface of the nanoparticle of the present invention is stabilized in a neutral state, the nonspecific adsorption of the nanoparticle due to ion bonding or intermolecular attraction is reduced under various environments.

In an embodiment of the present invention, the adsorptivity of a fluorescent nanoparticle such as a quantum dot to an adherend such as a cell membrane or a plastic surface, particularly, an electrostatically-charged adherend is remarkably weakened because its nonspecific adsorption is reduced after its surface is provided with amphoteric ion molecules.

In an aspect of the present invention, there is provided a nanocomposite, comprising: a nanoparticle including amphoteric ion molecules formed on a surface thereof; and a specific bonding material bonded to the nanoparticle.

In the present invention, the specific bonding material refers to a material inducing specific bonding between a nonoparticle and an external material. For example, the specific bonding material may be an antigen, an antibody, a probe, or the like.

In the present invention, the nanoparticle can be usefully used as a fluorescent body or a carrier. In an embodiment of the present invention, the nanoparticle of the nanocomposite may be a fluorescent, light-absorbing or light-emitting nanoparticle, for example, a nanosized quantum dot. In this case, the nanocomposite is bonded to a specific material by the specific bonding material without nonspecific adsorption of a nanoparticle, and then produces fluorescence, absorbs light and emits light. In the case of using the unique optical properties of the nanoparticle, the nanoparticle can be used for a contrast agent for magnetic resonance imaging or in vivo near-infrared fluorescence imaging. When amphoteric ion molecules are applied to the surface of a nanoparticle, a nanoparticle having minimized non-specific adsorption can be realized. In this case, there is an advantage in that only an object to be imaged can be selectively observed by minimizing the non-specific adsorption of a nanoparticle to be used as a marker for imaging.

In another embodiment of the present invention, the nanoparticle of the nanocomposite may be a nanosized carrier including a physiological material, a pharmaceutical material or a pharmaceutical composition. In this case, the nanocomposite can be selectively carried or bonded to the site requiring a pharmaceutical or physiological material by a specific bonding material.

In an aspect of the present invention, there is provided a method of preparing an amphoteric ion nanoparticle by reacting a nanoparticle with amphoteric ion molecules in a dispersion medium.

In the present invention, the dispersion medium may be an organic solvent, water or a mixture thereof, and the amphoteric ion molecules are reacted with the nanoparticle dispersed in the dispersion medium by a ligand substitution method or the like.

In another aspect of the present invention, there is provided an amphoteric ion molecule of Formula (I) below:

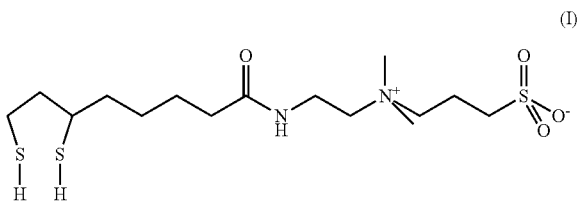 [SMILES: C[N+](C)(CCCS(=O)(=O)[O-])CCNC(=O)CCCCC(S)CCS]

(I)

In still another aspect of the present invention, there is provided a method of preparing the amphoteric ion molecule of Formula (I) above, as shown in FIG. 2.

In still another aspect of the present invention, the present invention is characterized in that amphoteric ion molecules are bonded to a surface to reduce the non-specific adsorption of the surface.

In the present invention, the term "surface" refers to a surface to which amphoteric ion molecules are bonded by various mechanical and chemical methods. For example, the surface may be a surface on which a glass thin film or a polymer thin film that can be bonded with amphoteric ion molecules are formed.

In an embodiment of the present invention, the surface may be a surface of a sensor. Here, the sensor may be a sensor for in vivo specific protein (for example, myoglobin, used to detect cardiac seizure) or a sensor for specific cell (for example, immune cells).

As described above, since the sensor provided on the surface thereof with amphoteric ion molecules has low non-specific bonding force, the non-specific adsorption of the sensor to other in vivo proteins is minimized, thus greatly increasing a signal/noise ratio that is one of the most important factors of a sensor.

Advantageous Effects

In the surface of a nanoparticle modified with an amphoteric ion molecule, the properties of the functional group of the molecule are not changed under the condition of a wide pH range or a high salt concentration. As a result, the amount of electric charge of the amphoteric ion molecule can be maintained at approximately 0, and the non-specific adsorption of the nanoparticle to proteins and phospholipids can be minimized.

MODE FOR INVENTION

Example 1

Synthesis of Amphoteric Ion Ligand

Figure 2:
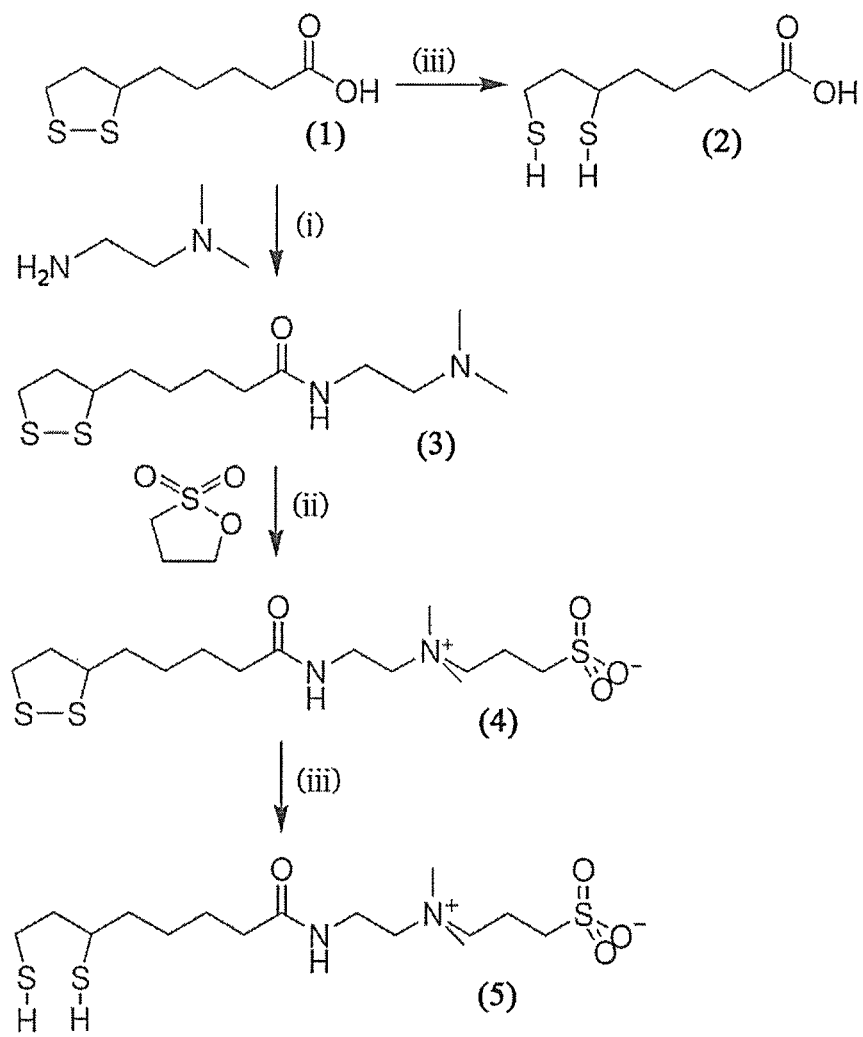
FIG. 2 shows a process of synthesizing an amphoteric ion molecule, wherein (i) carbonyl diimidazole, N,N-dimethylethylenediamine/anhydrous chloroform; (ii) 1,3-propanesultone/anhydrous chloroform; and (iii) sodium borohydride/deionized water.

Lipoic acid ((1) of FIG. 2) was dissolved in anhydrous chloroform, 1.3 equivalents of carbonyldiimidazole was added thereto, the solution was stirred for 5 minutes at room temperature under a vacuum atmosphere, and then a reaction solution layer, excluding the remaining carbonyldiimidazole, was separated. Subsequently, N,N-dimethylethylenediamine corresponding to 5 equivalents of lipoic acid was dissolved in anhydrous chloroform under a nitrogen atmosphere, cooled by an ice bath, and then added to the above solution to obtain a mixed solution. The mixed solution was stirred for 1 hour to obtain a reaction solution (resultant product ((3) of FIG. 2)). The reaction solution was purified with a 10% NaCl aqueous solution three times and purified with distilled water one time. Then, 1,3-propanesultone was added to the purified reaction solution, and this mixed solution was stirred at room temperature for 24 hours to obtain a solid (resultant product ((4) of FIG. 2)), and then the obtained solid was filtered. The filtered solid was dissolved in an aqueous solution, its pH having been adjusted to 9 by using 2N NaGH, and then 2 equivalents of $NaBH_4$ were added to the aqueous solution, and then this mixed solution was stirred at room temperature for 4 hours to synthesize an amphoteric ion ligand ((5) of FIG. 2). The synthesized amphoteric ion ligand was directly used without being purified.

Synthesis of Nanoparticle

The nanoparticle synthesis method disclosed in the present specification is one of various synthesis methods, and is not limited thereto. Synthesis of a quantum dot, which is one of various types of nanoparticles, was performed as follows. Octadecene and oleylamine was introduced into a round-bottom flask, and then the flask was heated to 100° C. while alternately changing between a vacuum state and a nitrogen-injected state, thereby making a nitrogen atmosphere filled with only nitrogen gas. Thereafter, the round-bottom flask was heated to 300° C., and then an octadecene solution containing cadmium (Cd) and selenium (Se) at a ratio of Cd:Se=1:5 was introduced into the high-temperature flask. Here, the ratio of Cd:Se may be adjusted according to the size of a desired nanoparticle. Thereafter, the flask, which is a reaction vessel, was slowly cooled to obtain nanoparticles dispersed in an organic solvent.

Example 2

Synthesis of Nanoparticle Surface-modified with Amphoteric Ion Molecules

Figure 1:
FIG. 1 is a schematic view showing an amphoteric ion molecule that is used as a surface modification molecule.
Figure 3:
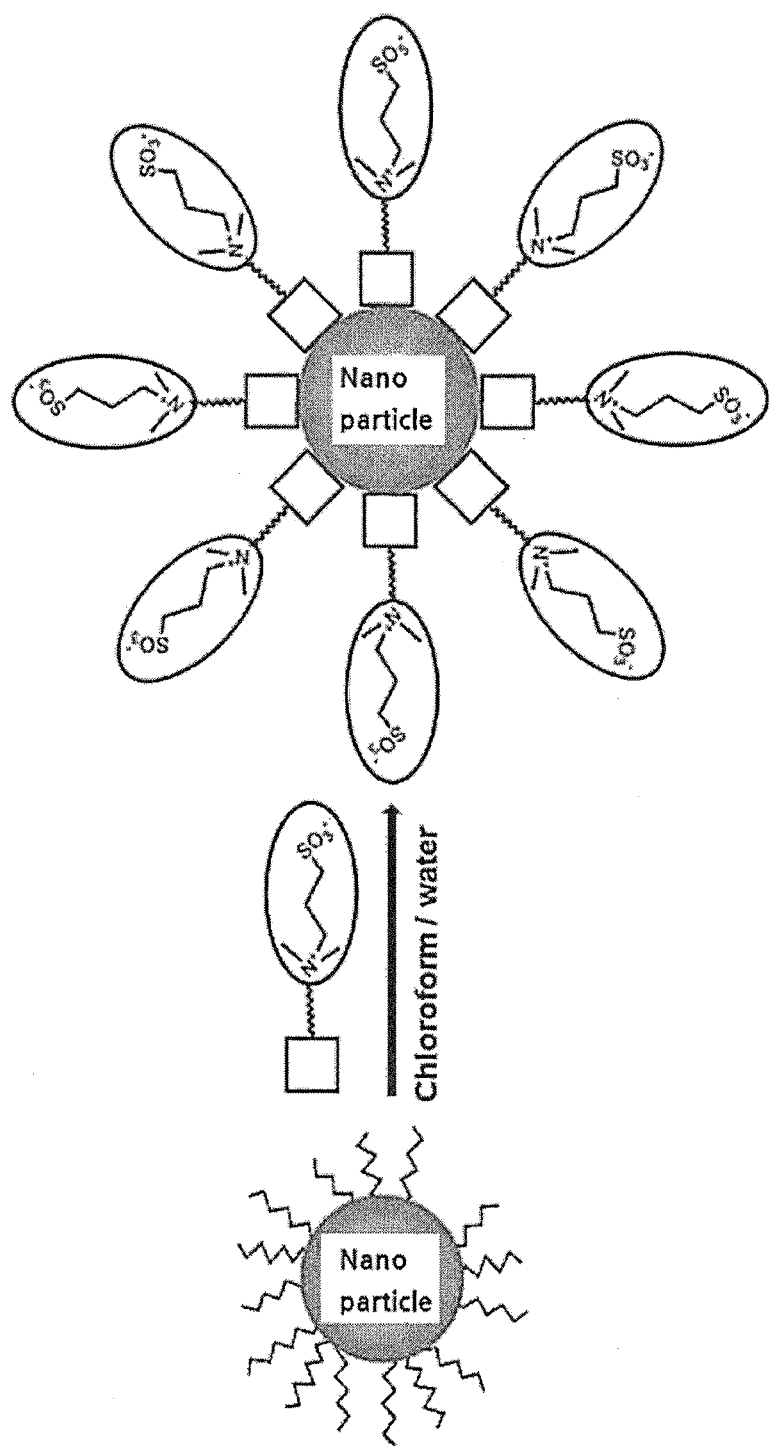
FIG. 3 is a schematic view showing a process of preparing a nanoparticle surface-modified with amphoteric ion molecules, wherein the surface-modified nanoparticle is prepared by surface-substituting the nanoparticle synthesized in an organic solvent with amphoteric ion molecules.

Nanoparticles synthesized in an organic solvent were dispersed in chloroform. An aqueous solution containing an excessive amount of the above-synthesized amphoteric ion molecules ((5) of FIG. 2) was mixed with the synthesized nanoparticles and then stirred at room temperature. Here, dithiol, which is one of the functional groups of the amphoteric ion molecule, has strong surface bonding force to a nanoparticle (quantum dot) compared to an organic molecule ligand containing phosphonic acid or primary amine as a functional group. Therefore, the organic molecule ligands bonded to the surface of the quantum dot were substituted with the amphoteric ion molecules, and simultaneously the quantum dots were moved to an aqueous solution layer, and thus quantum dots were dispersed in the aqueous solution. Thereafter, a chloroform layer was separated and removed, and only the aqueous solution layer was dialyzed to remove residual ligands. FIG. 3 shows amphoteric ion molecules schematized as in FIG. 1. As shown in FIG. 3, the surface bonding region of each of the amphoteric ion molecules is indicated by a square, the connection region thereof is indicated by a wave-shaped line, and the functional group region thereof is indicated by an ellipse.

Example 3 (Comparative Example 1)

Synthesis of Nanoparticle Surface-modified with Molecules Having Carboxy Group (—COOH)

Figure 4:
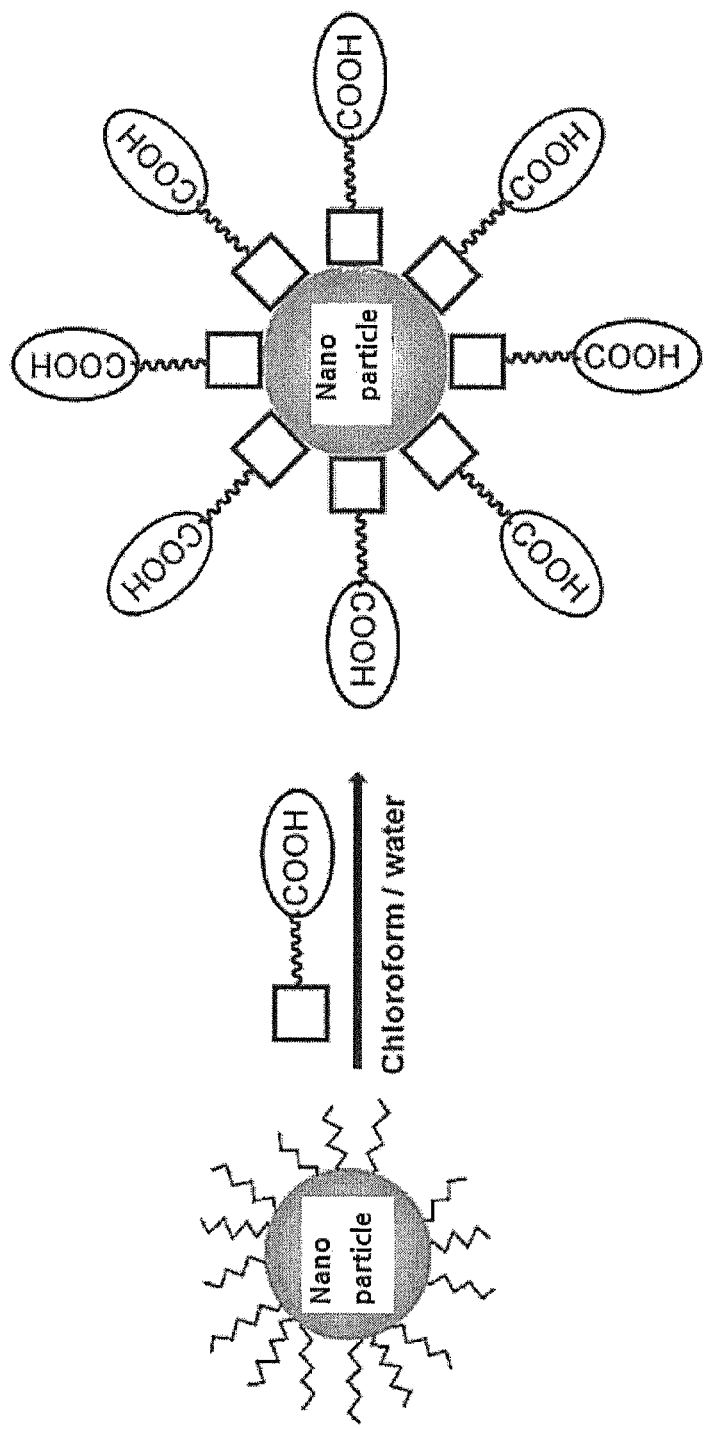
FIG. 4 is a schematic view showing a process of preparing a surface-modified nanoparticle, wherein the surface-modified nanoparticle is prepared by surface-substituting the nanoparticle synthesized in an organic solvent with carboxy-containing molecules.

Nanoparticles synthesized in an organic solvent were dispersed in chloroform. An aqueous solution containing an excessive amount of the above-synthesized molecules having a carboxy group ((2) of FIG. 2) was mixed with the purified quantum dots and then stirred at room temperature. In this case, the organic molecule ligands bonded to the surface of the quantum dot were substituted with the molecules having a carboxy group, and simultaneously the quantum dots were moved to an aqueous solution layer, and thus quantum dots were dispersed in the aqueous solution. Thereafter, a chloroform layer was separated and removed, and only the aqueous solution layer was dialyzed to remove residual ligands. FIG. 4 shows carboxy group-containing molecules schematized as in FIG. 1. As shown in FIG. 4, the surface bonding region of each of the carboxy group-containing molecules is indicated by a square, the connection region thereof is indicated by a wave-shaped line, and the function group region thereof is indicated by an ellipse.

Example 4

Figure 5:
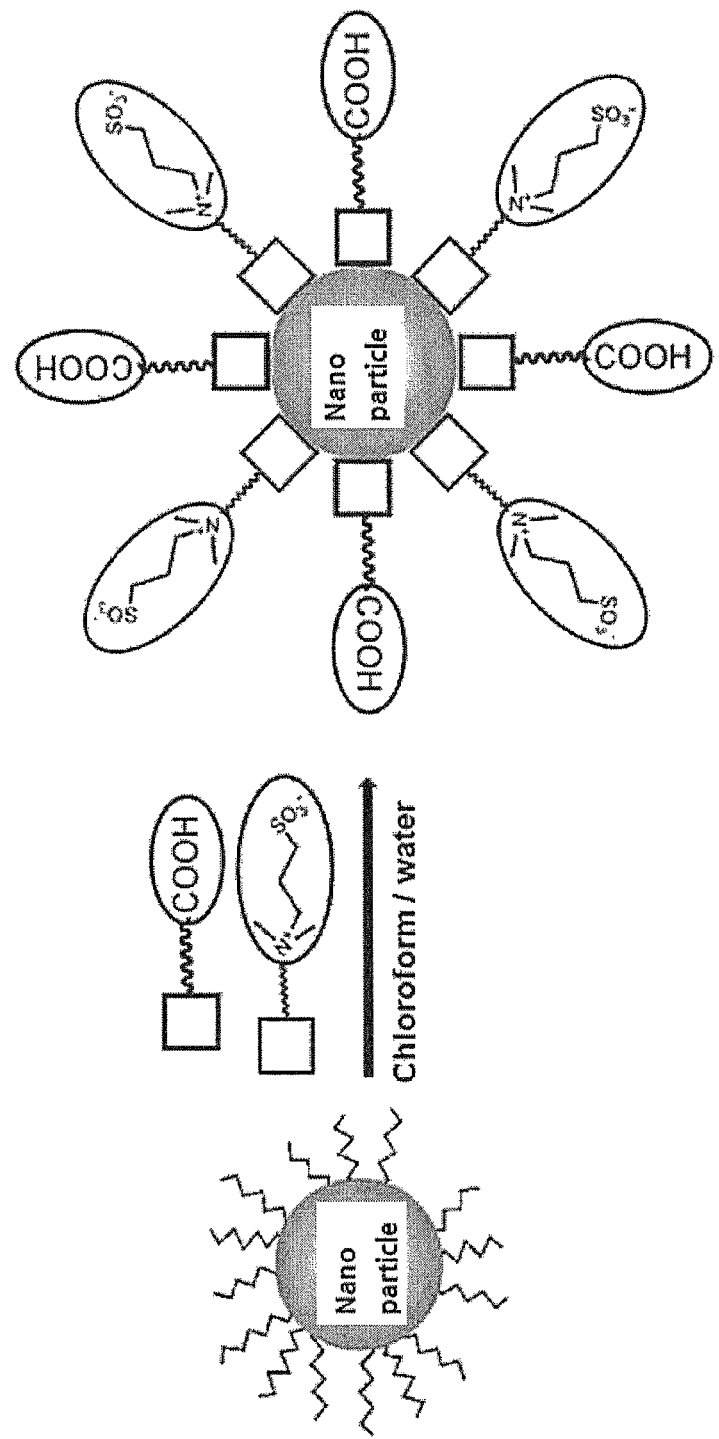
FIG. 5 is a schematic view showing a process of preparing a surface-modified nanoparticle, wherein the surface-modified nanoparticle is prepared by simultaneously surface-substituting the nanoparticle synthesized in an organic solvent with amphoteric ion molecules and carboxy-containing molecules.
Figure 6:
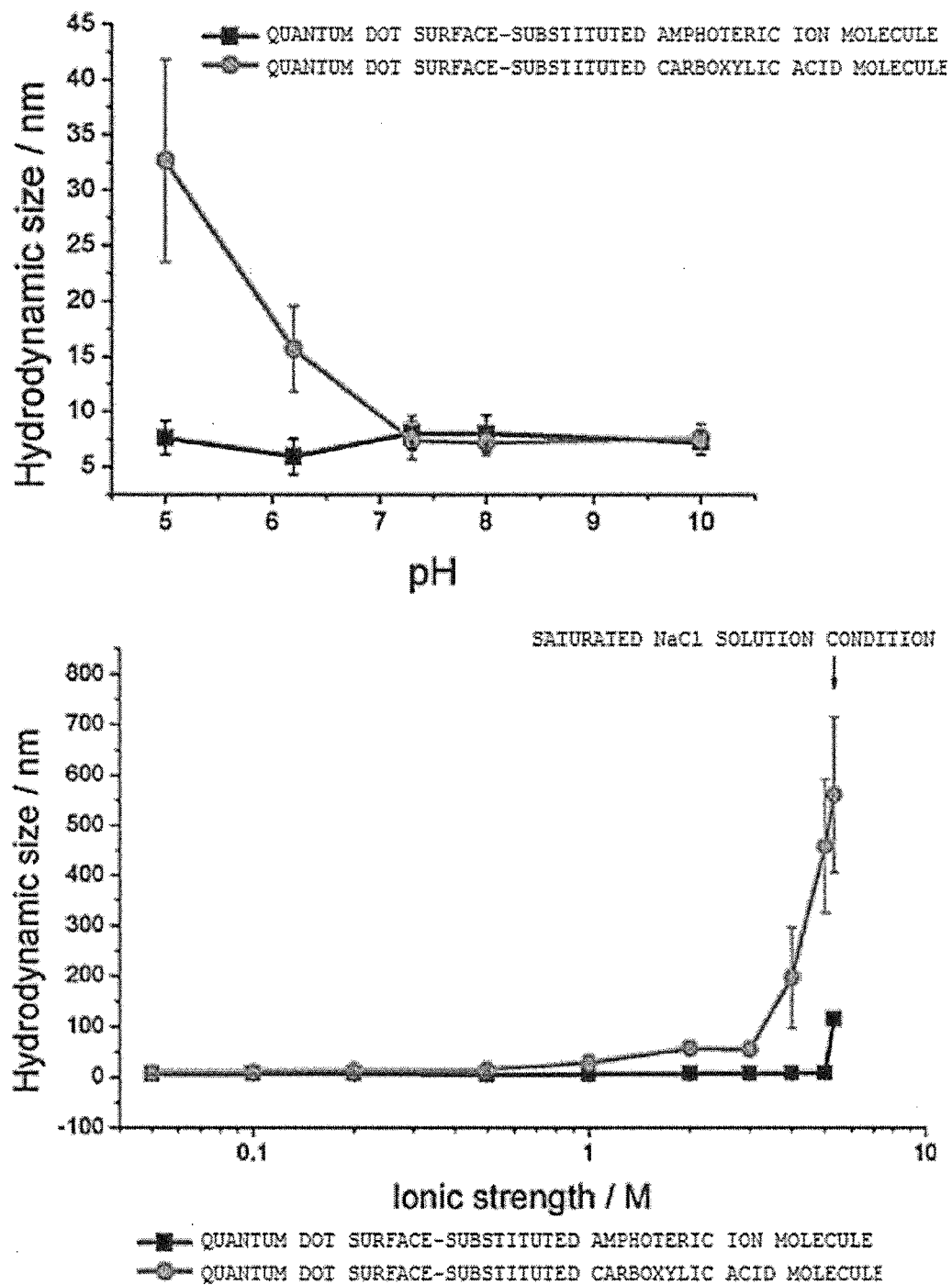
FIG. 6 shows the size of a hydrated quantum dot according to the pH change (pH: 5~10) at the left side of FIG. 6, and shows the size of a hydrated quantum dot according to the salt concentration change (ionic strength: 0.05~5 M) at the right side thereof, wherein, as the size of the hydrated quantum dot increases, the hydrated quantum dot becomes unstable, so the hydrated quantum dot is not uniformly dispersed in an aqueous solution to be agglomerated, thereby decreasing the possibility of application of the quantum dot.

Synthesis of Nanoparticle Surface-modified with both Amphoteric Ion Molecules and Molecules Having Carboxy Group Nanoparticles synthesized in an organic solvent were dispersed in chloroform. An aqueous solution containing an excessive amount of the above-synthesized amphoteric ion molecules ((5) of FIG. 2) and molecules having a carboxy group ((2) of FIG. 2) was mixed with the purified quantum dots and then stirred at room temperature. In this case, the organic molecule ligands bonded to the surface of the quantum dot were substituted with both the amphoteric ion molecules and the molecules having a carboxy group, and simultaneously the quantum dots were moved to an aqueous solution layer, and thus quantum dots were dispersed in the aqueous solution. Thereafter, a chloroform layer was separated and removed, and only the aqueous solution layer was dialyzed to remove residual ligands. FIG. 5 shows surface molecules schematized as in FIG. 1. As shown in FIG. 5, the surface bonding region of each of the surface molecules is indicated by a square, the connection region thereof is indicated by a wave-shaped line, and the function group region thereof is indicated by an ellipse.

Example 5

Measurement of Size of Hydrated Nanoparticle Surface-modified with Amphoteric Ion Molecule According to Change in pH and Salt Concentration When a nanoparticle is surface-modified with amphoteric ion molecules having a functional group region, the surface-modified nanoparticle exhibits the properties of the functional group region of the amphoteric ion molecule. For this purpose, the size of the hydrated nanoparticle substituted with amphoteric ion molecules as in Example 2, and the size of the hydrated nanoparticle substituted with molecules having a carboxy group (—COOH) as in Example 3 were measured. Here, a quantum dot was used as the nanoparticle. The quantum dot is characterized in that it receives light and then emits light having a specific wavelength. The size of each hydrated quantum dots is about 6~7 nm when they are uniformly dispersed in a solution.

In the case (Example 2) of the nanoparticle substituted with amphoteric ion molecules, the change in size of the hydrated nanoparticle according to the changes in pH and salt concentration was rarely observed. However, in the case (Example 3) of the nanoparticle substituted with molecules (control group) having a carboxy group (—COOH) as a functional group region, the change in size of the hydrated nanoparticle according to the changes in pH and salt concentration was clearly observed. As a result, it can be ascertained that amphoteric ion molecules can stabilize the surface of a nanoparticle in wide pH and salt concentration ranges compared to the control group. The fact that the size of the hydrated nanoparticle is maintained constant means that amphoteric ion molecules can effectively disperse and stabilize nanoparticles under various aqueous solution conditions.

Example 6

Evaluation of Degree of Non-specific Adsorption of Nanoparticle to Polymer Bead

Figure 7:
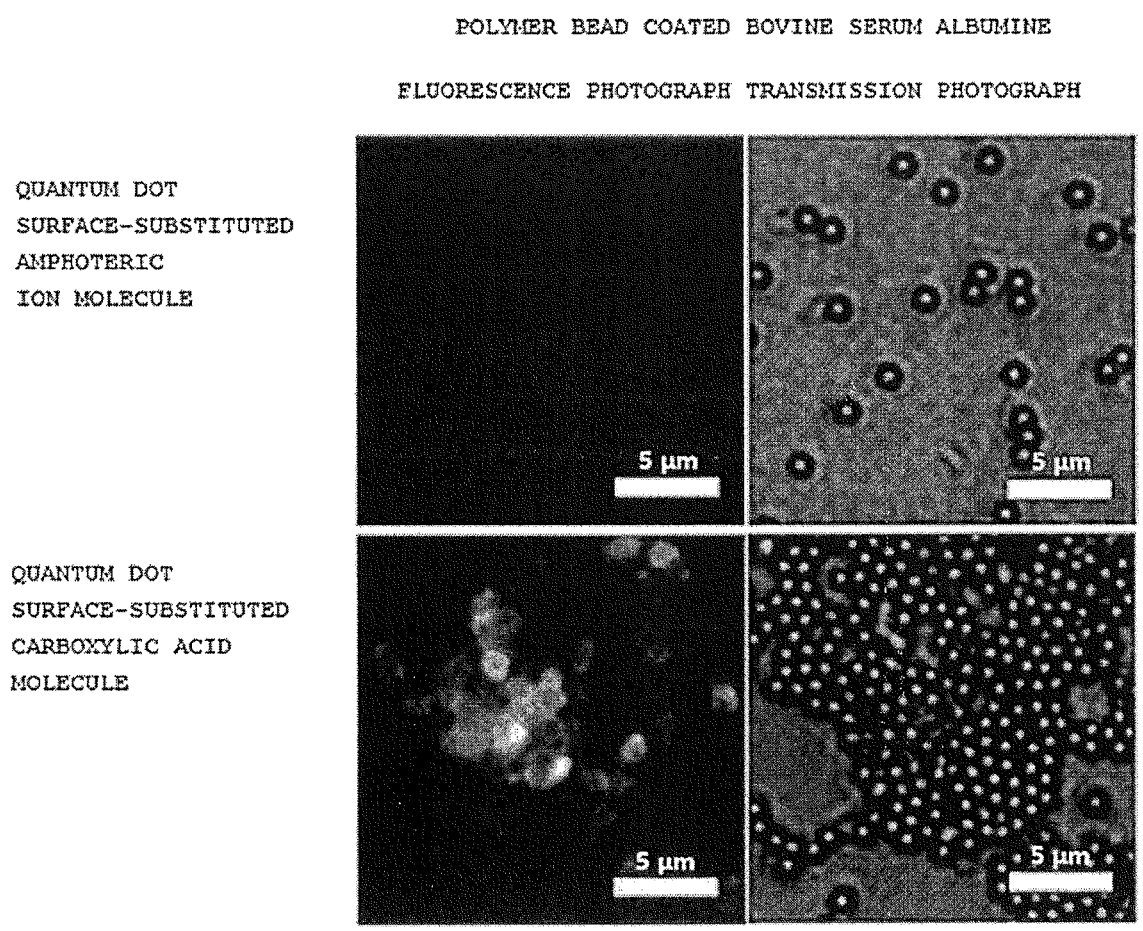
FIG. 7 is a fluorescence microscope photograph for observing nonspecific bonding between a quantum dot and a polymer bead, wherein the scale bar=5 μm.

FIG. 7 shows the result that the non-specific bonding between the nanoparticle (Example 2) substituted with amphoteric ion molecules and polymer beads was weakened due to the surface substitution of amphoteric ion molecules. Generally, in portable substrate-based sensors, such as DNA array assay, Lab on a chip, and the like, the surface of a substrate is coated with biomolecules such as bovine serum albumin in order to reduce the degree of non-specific adsorption. However, non-specific bonding does not completely disappear, and somewhat appears even on the substrate surface treated in this way.

Therefore, the present inventors intended to ascertain whether or not the non-specific adsorption of nanoparticles on the polymer surface realized in a similar manner to above was reduced. First, polymer beads coated with bovine serum albumin were mixed with nanoparticles, residual quantum dots were sufficiently washed, and then the fluorescence of the nanoparticles (that is, quantum dots) non-specifically adsorbed on the surface of the polymer beads was observed by a fluorescence microscope.

Since the nanoparticles surface-substituted with molecules having a carboxy group (—COOH) as a functional group region are easily adsorbed on the surface of polymer beads, it can be ascertained that the fluorescence of the nanoparticles (that is, quantum dots) adsorbed on the surface of the polymer beads was observed. However, in the case of the quantum dots surface-substituted with amphoteric ion molecules, the fluorescence thereof was barely observed. Consequently, it can be ascertained that, since the nanoparticles were neutrally charged, electrostatic attraction was minimized, and thus the degree of non-specific adsorption was remarkably lowered.

Example 7

Evaluation of Degree of Non-specific Bonding of Nanoparticle to Living Cell

Figure 8:
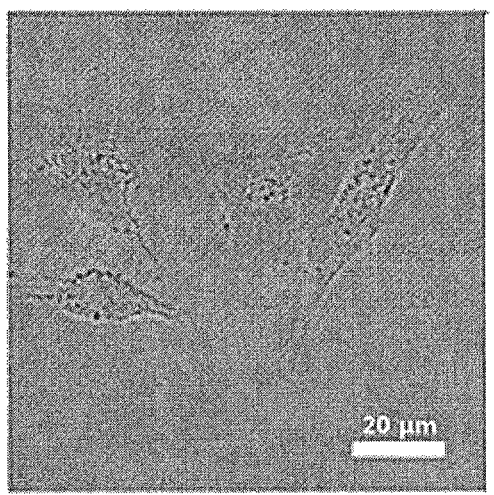
FIG. 8 is a confocal microscope photograph of a cervical cancer cell cultured with a quantum dot, wherein the green colored portion of the photograph shows a quantum dot, and the scale bar=20 μm.
Figure 8:
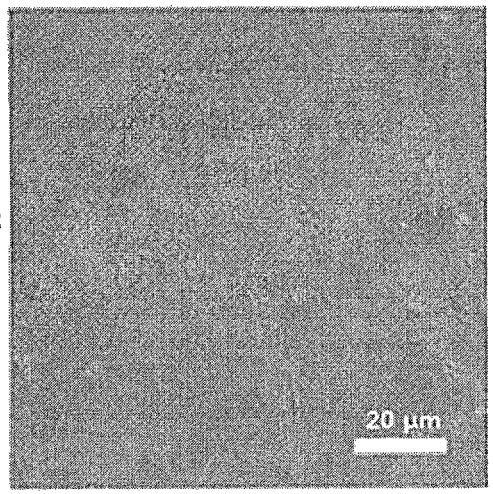

FIG. 8 shows confocal microscope photographs of cervical cancer cells respectively treated with the quantum dots (Example 2) surface-substituted with amphoteric ion molecules and the quantum dots (Example 3) surface-substituted with molecules having a carboxy group. Here, the green colored portion of each of the photographs is a portion at which the fluorescence of the quantum dots was observed. Each of the photographs selectively shows only the fluorescence emitted from the cells.

Similarly to the result mentioned in Example 6 above, it was ascertained that the non-specific adsorption of the nanoparticles (Example 2) substituted with amphoteric ion molecules to the polymer beads was reduced. Consequently, it can be ascertained that the fluorescence of quantum dots on the inner and outer walls of the cells was not observed when the quantum dots were substituted with amphoteric ion molecules compared to when the quantum dots (control group) were substituted with molecules having a carboxy group.

In the case of the nanoparticles substituted with amphoteric ion molecules, endocytosis due to the non-specific adsorption of the noanopaticles on the inner and outer walls of the cells was not observed because interaction between the nanoparticles and the cells can be controlled by the electrostatic attraction therebetween. However, in the case of the nanoparticles (control group) substituted with molecules having a carboxy group, the nonspecific bonding of the nanoparticles to the cells was observed, and thus the endocytosis was also observed. From these results, it can be ascertained that, when the degree of non-specific adsorption of quantum dots to cells is remarkably lowered by using amphoteric ion molecules, these amphoteric ion molecules can be used in nanoparticle surface modification technologies for developing bioimaging technologies.

Example 8

Figure 9:
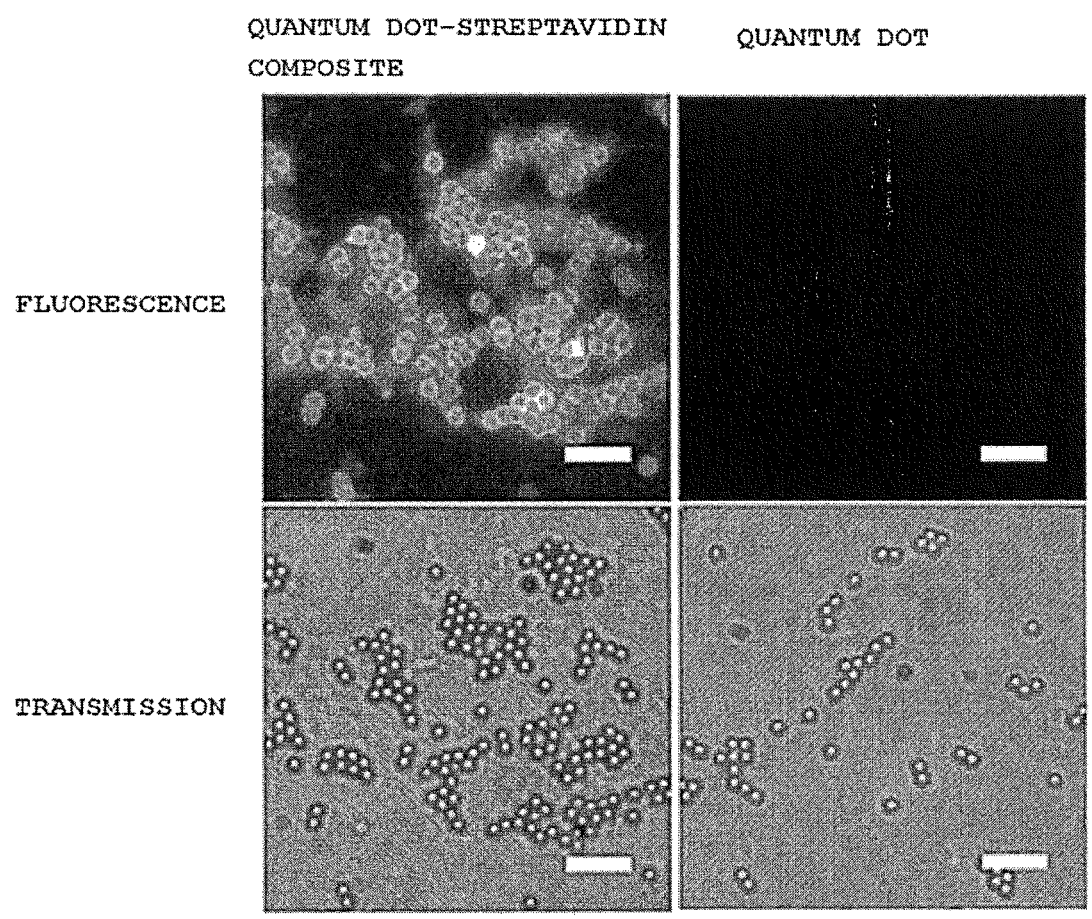
FIG. 9 shows fluorescence and transmission imaging photographs of biotin-coated polymer beads marked with a quantum dot-streptavidin composite, wherein the yellow colored portion of each of the photographs shows a quantum dot, and is a fluorescent signal which is one of specific optical properties of a quantum dot.

Evaluation of Selective Marking Ability of Nanoparticle Using Quantum Dot-protein Composite The nanoparticle (Example 4) surface-substituted with both molecules having a carboxy group and amphoteric ion molecules may be formed into a composite by strong covalent bonding due to the biological conjunction with streptavidin that is one of biomolecules. In the present specification, a quantum dot was given as an example of nanoparticles, and streptoavidin was given as an example of a protein. Therefore, in the present invention, a quantum dot-streptoavidin composite was synthesized by the biological junction of a quantum dot and streptoavidin. FIG. 9 shows fluorescence and transmission imaging photographs of biotin-coated polymer beads mixed with a quantum dot-streptavidin composite. Strong intermolecular attraction (for example, bonding between an antibody and an antigen), that is, strong attraction force due to multiple hydrogen bonds, is applied between streptavidin and biotin. Therefore, biotin-coated polymer beads can be marked with streptavidin, and thus can also be marked with a quantum dot-streptavidin composite. When the quantum dots (control group) synthesized in Example 4 were mixed with biotin-coated polymer beads without being formed into quantum dot-streptavidin composites, the degree of non-specific adsorption of the quantum dots became low due to amphoteric ion molecules of the surface of the quantum dots, and thus fluorescence of the quantum dots was not observed.

The invention claimed is:

1. A nanoparticle, surface-modified with an amphoteric ion molecule of Formula (I) below:

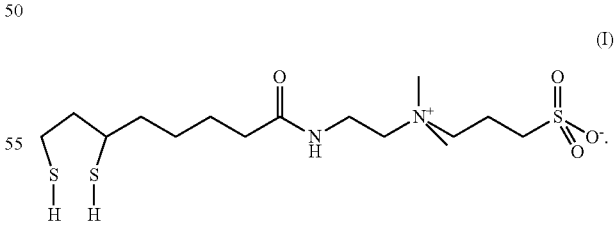

(I)

2. The nanoparticle of claim 1, wherein the nanoparticle is surface-substituted with the amphoteric ion molecule.

3. The nanoparticle of claim 1, wherein the nanoparticle is made of a metal, a nonmetal, ceramic, plastic, a polymer, a semiconductor, a quantum dot or at least one composite material thereof.

4. The nanoparticle of claim 1, wherein the nanoparticle is a nanoparticle having optical properties.

5. The nanoparticle of claim 1, wherein the nanoparticle is a fill-type nanoparticle whose inside is filled, or a cavity-type nanoparticle whose inside is at least partially provided with a space.

6. The nanoparticle of claim 1, wherein a length of the amphoteric ion molecule is smaller than an outer diameter of the nanoparticle.

7. A method of preparing a nanoparticle surface-modified with an amphoteric ion molecule by reacting a nanoparticle with an amphoteric ion molecule of Formula (I) below:

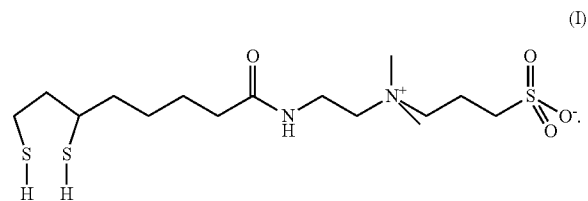

(I)

8. The method of claim 7, wherein, before the reaction with the amphoteric ion molecule, the nanoparticle is provided on a surface thereof with a ligand that can be substituted with the amphoteric ion molecule, and the ligand is substituted with the amphoteric ion molecule.

9. The method of claim 7, wherein, before the reaction with the amphoteric ion molecule, the nanoparticle is a nanoparticle dispersed in a dispersion medium selected from among an organic solvent, water and a mixture thereof.

10. A nanoparticle, surface-modified with an amphoteric ion molecule of Formula (I) below and a molecule having a carboxy group:

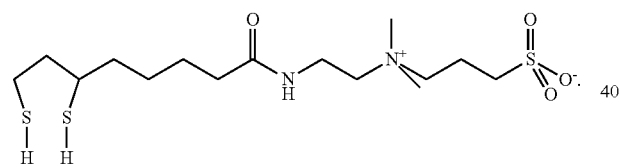

(I)

11. An amphoteric ion molecule, having a structure of Formula (I) below:

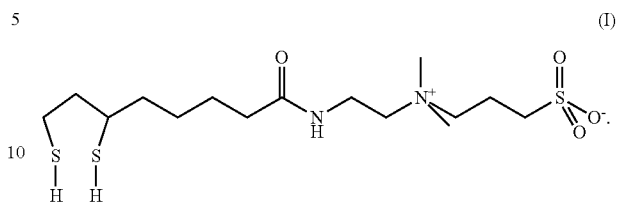

(I)

12. A method of preparing the compound of claim 11, represented by Formula (I) above, by reacting a compound of Formula (IV) below with sodium borohydride:

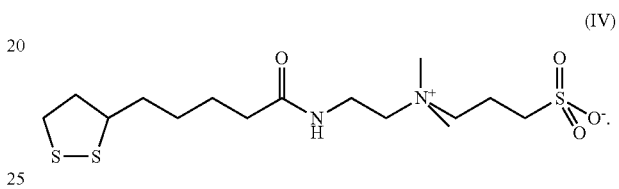

(IV)

13. The method of claim 12, wherein the compound of Formula (IV) above is prepared by reacting a compound of Formula (II) below with a compound of Formula (III) below:

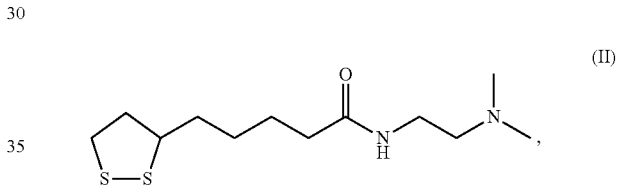

* * * * *